(12) United States Patent
Wenckens

(10) Patent No.: US 8,241,660 B2
(45) Date of Patent: Aug. 14, 2012

(54) PATCH FOR THE EXPULSION OF INSECT POISON FROM THE SKIN AFTER STINGS FROM MEMBRANOUS INSECTS (HYMENOPTERA)

(76) Inventor: Martin Wenckens, Lejre (DK)

( * ) Notice: Subject to any disclaimer, the term of this patent is extended or adjusted under 35 U.S.C. 154(b) by 613 days.

(21) Appl. No.: 12/377,796

(22) PCT Filed: Aug. 20, 2007

(86) PCT No.: PCT/IB2007/002386
§ 371 (c)(1),
(2), (4) Date: Feb. 17, 2009

(87) PCT Pub. No.: WO2008/023237
PCT Pub. Date: Feb. 28, 2008

(65) Prior Publication Data
US 2010/0297205 A1     Nov. 25, 2010

(30) Foreign Application Priority Data

Aug. 23, 2006 (DK) ........................ PA 2006 01095
May 11, 2007 (DK) ........................ PA 2007 00706

(51) Int. Cl.
| A61K 9/70 | (2006.01) |
| A61F 13/00 | (2006.01) |
| A61L 15/16 | (2006.01) |
| A61F 13/02 | (2006.01) |
| A61K 35/24 | (2006.01) |
| A61K 35/37 | (2006.01) |
| A61K 31/16 | (2006.01) |
| A61K 31/24 | (2006.01) |
| A61K 31/70 | (2006.01) |
| A61K 31/715 | (2006.01) |
| A61K 47/00 | (2006.01) |

(52) U.S. Cl. ........ 424/443; 424/445; 424/446; 424/447; 424/448; 424/537; 514/25; 514/53; 514/535; 514/537; 514/626; 514/769; 514/781; 514/816; 514/817; 514/818; 514/830

(58) Field of Classification Search .................. 424/443, 424/445, 446, 447, 448; 514/830
See application file for complete search history.

(56) References Cited

U.S. PATENT DOCUMENTS

| 5,823,983 | A | 10/1998 | Rosofsky et al. |
| 6,120,792 | A | 9/2000 | Juni |
| 6,528,086 | B2 * | 3/2003 | Zhang .......................... 424/449 |
| 6,660,901 | B2 * | 12/2003 | Church .......................... 602/48 |
| 7,338,673 | B2 | 3/2008 | Ferrell, Jr. et al. |
| 2001/0055608 | A1 | 12/2001 | Hymes et al. |
| 2006/0057189 | A1 * | 3/2006 | Ferrell, Jr. ..................... 424/443 |

FOREIGN PATENT DOCUMENTS

| WO | WO-00/09176 | 2/2000 |
| WO | WO 00/69405 | 11/2000 |
| WO | WO-01/41746 | 6/2001 |
| WO | WO-03/034900 | 5/2003 |

OTHER PUBLICATIONS

Judith A. Marlett and Milton H. Fischer, "The active fraction of psyllium seed husk", Proceedings of the Nutrition Society (2003), 62, 207-209.*
R. de la Burde, F. Crayton and A. Bavley, "Fate of Carbohydrates during Thermal Degradation of Tobacco", Nature (1962), 196, 166-167.*

* cited by examiner

*Primary Examiner* — John Pak
*Assistant Examiner* — Nathan W Schlientz
(74) *Attorney, Agent, or Firm* — Gifford, Krass, Sprinkle, Anderson & Citkowski, P.C.

(57) ABSTRACT

This invention relates to a patch for the expulsion of insect poison from the skin after stings from membranous insects (Hymenoptera). The patch is characterized in comprising a poison-aspirating matrix comprising an expulsion agent as well as a swell layer, which swells after the addition of a liquid through a hole on the top of the patch and thus adds a light pressure to the poison-aspirating matrix towards the skin, whereby a local and relieving effect is achieved. In one embodiment, the matrix further comprises a local anesthetic. The expulsion agent is e.g. a carbohydrate. The swell layer consists e.g. of a silica gel.

9 Claims, 1 Drawing Sheet

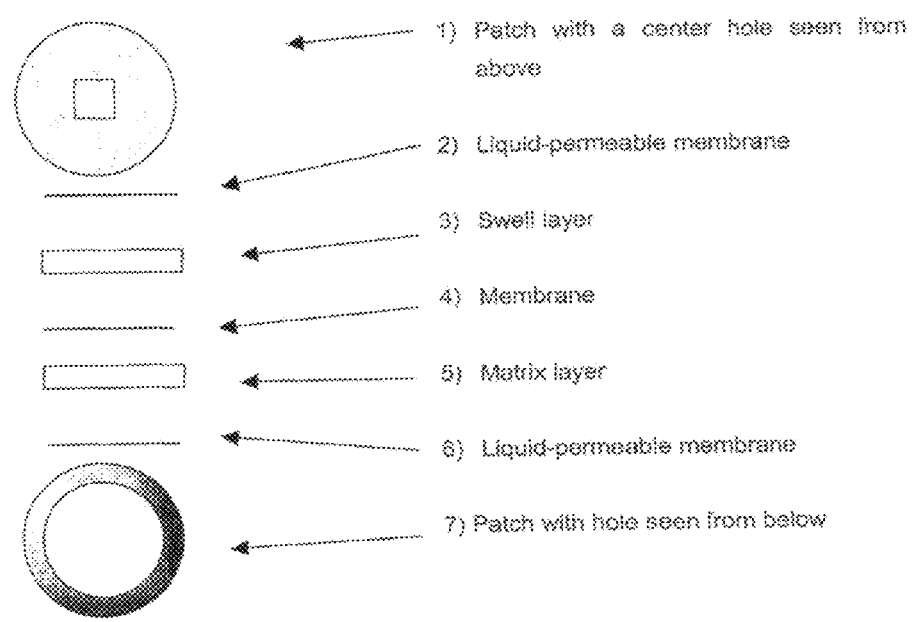

PATCH FOR THE EXPULSION OF INSECT POISON FROM THE SKIN AFTER STINGS FROM MEMBRANOUS INSECTS (HYMENOPTERA)

FIELD OF THE INVENTION

The invention relates to a patch comprising an expulsion agent for the expulsion of poison from the skin after stings from membranous insects.

BACKGROUND OF THE INVENTION

Of the membranous insects with a poisonous stinger in Denmark, there are about 250 different kinds of bees, 20 different kinds of bumblebees, and between 4,000 and 5,000 different types of wasps, of which half a dozen hornets as well as ichneumon wasps and spider wasps have a poisonous stinger.

Each summer, these membranous insects cause much irritation and fear both in children and adults, who fear the stings of these insects. In Denmark, each year 10,000 patients are treated for insect stings, of which on average 2 patients die.

Membranous insects such as bees, wasps and hornets use their poisonous stinger as part of their defense. When the insect stings, poison is pumped out of the stinger and into the skin. The stings are always unpleasant and result after a few minutes to hours in swelling, flushing, pain, and skin irritation as well as itching that may last up to a week. Several stings, or a single sting in the case of an allergic person, can cause hazardous conditions such as anaphylactic shock with symptoms such as a swelling of the tongue, a drop in the blood pressure, respiratory distress, abdominal pain, nettle rash, vomiting and diarrhea. Bee poison contains a composition of acid fluids, which contain i.a. histamine and mellitine as well as enzymes that enhance the effect of the poison. The poison increases the blood flow to the sting wound and dissolves the red blood cells resulting in pain and a flushing of the sting wound. Bees are capable of attacking in swarms, which can pursue their victim and give the attacked person up to a dozen stings. The poison of the hornet is alkaline and contains more histamine than the poison of the bee, as well as serotonin, which is not contained in the poison of the bee. Due to the potency of the poison, it can be potentially lethal to small children of the age of 4 to 5 to get stung.

There are known methods for avoiding the unpleasant effects of insect stings such as to apply a local anesthesic onto the skin. This treatment only offers pain relief and does not remove the poison from the sting, which is desirable in order to reduce a potential allergic reaction.

Methods for removing the poison comprises different types of exhaust equipment such as e.g. the commercially available Giftsuger®. The end of such exhausters is placed over the sting to create a vacuum that absorbs the poison. The disadvantages of this method are that additional mechanical and painful stress is added to the already soar area, that only one sting can be treated at a time, and that the equipment as such can be inconvenient to bring in a bag or a pocket.

An old household remedy is to place a sugar cube on the stung area, by which the sugar will draw out the poison by means of osmosis. The disadvantages of this method is that the sugar cube quickly crumbles or partly dissolves and that the sugar cube is to be held on to the skin with a certain pressure which limits the method to only relieve one or two stings at a time. In addition to this, it is not desirable to a stung person to be in contact with sugar as such, since the insects are attracted to the sugar, which implies the risk of additional stings.

It has not been described previously to use patches for the extraction or expulsion of insect poison. However, patches that can exert pressure or that contain a local anesthetic have been used for open wounds and bites.

U.S. Pat. No. 5,823,983 relates to a patch with a swell layer, where blood or another liquid will make the layer swell and thus exert pressure on the wound at the same time as aspirating the blood. The patch is not suitable for bee stings, as it does not contain an agent, which can draw out poison.

WO03034900 relates to a patch containing anesthetics designed for open wounds. The patch is not suitable for bee stings, as it does not contain an agent, which can draw out poison and as the pressure required is not achieved.

WO0009176 relates to a patch, which can aspirate liquid from a wound by means of adsorption based on carbohydrates with the aim of reducing the healing period. Besides, the patch contains antibiotics and antiseptics and is thus primarily suitable for open wounds.

U.S. Pat. No. 6,120,792 relates to a patch with anesthetics and a liquid-aspirating layer. The patch is not suitable for insect stings, as it does not contain an agent, which can expel insect poison.

SUMMARY OF THE INVENTION

The present invention provides for the first time a patch that can expel or extract poison from insect stings. The patch comprises a poison-aspirating matrix with an expulsion agent that can expel the poison, where this expulsion agent is only available for the stung area, for which reason, if this agent e.g. comprises a carbohydrate, it does not attract more insects, at the same time as achieving a light pressure of the poison-aspirating matrix on the sting due to a swell layer, which enhances the effect of the expulsion. By using several patches, a simultaneous treatment of several stings can be achieved, either as one patch at a time on each stung area or with a larger patch, which can cover more stings at one time. By encasing the poison-aspirating matrix and the swell layer in a patch, a local and stable impact of the stung skin area is achieved. In one embodiment of the invention, the matrix layer contains local anesthetics, which further produces a relieving effect.

EXPLANATION OF FIGURES

FIG. 1 illustrates the structure of a patch according to the invention seen from above (1), the different layers of a patch according to the invention (1-6), and a patch according to the invention seen from below (7).

DETAILED DESCRIPTION OF THE INVENTION

A patch according to the present invention is characterized in comprising:
- an outer layer, which is larger than and covers the other subjacent layers of the patch, and which comprises an adhesive or an adhesive layer on at least that part of the underside of this outer layer, which is in contact with the skin, (cf. FIG. 1, 1)
- a matrix layer comprising a poison-expelling agent (cf. FIG. 1, 5)
- as well as a removable protective layer (not illustrated on FIG. 1)

In preferred embodiments, a patch according to the present invention is characterized in comprising:

- an outer layer, which is larger than and covers the other subjacent layers of the patch, and which comprises an adhesive or an adhesive layer on at least that part of the underside of this outer layer, which is in contact with the skin, and which outer layer is further characterized in comprising one or several holes, through which liquid can be added to one or more of the subjacent layers of the patch (cf. FIG. 1, 1)
- a permeable membrane, which allows liquid to penetrate into the subjacent swell layer (cf. FIG. 1, 2)
- a swell layer (cf. FIG. 1, 3)
- a membrane, which separates the swell layer from a subjacent matrix layer (cf. FIG. 1, 4)
- a matrix layer comprising a poison-expelling agent (cf. FIG. 1, 5)
- optionally, a permeable membrane consisting of gauze or the like, which allows the insect poison to penetrate into the matrix layer and which, together with the membrane (cf. FIG. 1, 4), completely or partly encases the matrix layer (cf. FIG. 1, 6)
- as well as a removable protective layer (not illustrated on FIG. 1)

Both the outer layer as well as the optional membrane, which separates the optional swell layer from the subjacent matrix layer, can be made of a breathable or an occluded material comprising polyvinyl acetate, polyvinyl idenchloride, polyethylene, polyurethane, polyester, ethylene vinyl acetate (EVA), polyethylene terephthalate, polybuthylene terephthalate, coated paper products, plate aluminum and the like, as well as a combination thereof. The outer layer can be a monolithic or multi-laminate layer and is either added an adhesive or is composed by a multi-laminate layer comprising an adhesive layer. The adhesive or adhesive layer is formed on the basis of standard prior art pressure-sensitive adhesives. Examples of pressure-sensitive adhesives include, but are not limited to, polyacrylates, polysiloxanes, polyisobutylene (PIB), polyisoprene, polybutadiene, styrene block polymers and the like. Examples of styrene block copolymer-based adhesives include, but are not limited to, styrene isoprene styrene block copolymers (SIS), styrene butadiene styrene copolymers (SBS), styrene ethylene buthene styrene copolymers (SEBS) and diblock analogues thereof. In certain embodiments, a plasticizer or an adhesive is added to the adhesive composition in order to improve the adhesive properties. Examples of suitable adhesives include, but are not limited to, aliphatic carbonhydrides, aromatic carbonhydrides, hydrogenerated esters, polyterpens, hydrogenerated wood resins, adhesive resins such as ESCOREZ, aliphatic carbonhydride resins manufactured by cationic polymerization of petro-chemical raw materials or thermal polymerization and a subsequent hydrogenisation of petro-chemical raw materials, resin ester adhesives and the like, mineral oil, as well as combinations thereof.

The optional membrane between the outer layer and an optional swell layer consists of a material that allows water or another liquid to penetrate into the optional subjacent swell layer. Thus, this material can be a permeable or semi-permeable membrane based on a polymeric material or the like.

The optional swell layer consists of a material that swells at the addition of water or another liquid, e.g. silica gel, compressed cellulose, a gel, comprised cellulose, calcium chloride, or combinations thereof.

The matrix layer comprising a poison-expelling agent, which—e.g. by means of osmosis—contributes to the extraction of the poison, comprises e.g. carbohydrates selected from the group consisting of sucrose, glucose, dextrose, maltose, or combinations thereof.

The optional permeable membrane consists of a material, which allows the insect poison to penetrate into the matrix layer, e.g. gauze or the like.

The removable protective layer is manufactured by a polymeric material and an optional metal coating. Examples of polymeric materials include polyurethane, polyvinyl acetate, polyvinylidenchloride, polypropylene, polycarbonate, polystyrene, polyethylene, polyethylene terephthalate, polybuthylene terephthalate, paper and the like, as well as a combination thereof.

Numerous different materials, which can be used in the manufacturing of the different layers of the patch according to the present invention, are described above. The invention includes the use of other materials than those specifically described here, including such materials, which may subsequently become prior art as being able to perform the necessary functions.

The effect of the structure of the patch is that the matrix layer comprising the poison-expelling agent, potentially via a permeable membrane, only gets in contact with the stung area where it should have an effect. In case the poison-expelling agent in the matrix layer comprises a carbohydrate, more bees will thus not be attracted.

The effect of the swell layer is that the matrix layer comprising the poison-expelling agent gets pressed down moderately towards the stung area, by which the poison is transported faster from the skin into the poison-expelling agent, which may be a carbohydrate.

In FIG. 1, the patch is illustrated with a round design, a core, which is in contact with the stung area, encircled by an adhesive edge. To a skilled person within the field it would, however, be obvious that a patch according to the invention can be shaped in any way known for patches, e.g. quadrangular, oval or as a traditional patch with a core flanked by two adhesive wings.

FIG. 1 further illustrates how the patch is constructed with several different layers with separate functions.

1) The patch seen from above. An outer layer manufactured by the same materials as traditional patches with a center hole, round, quadrangular or another shape, through which a few drops of liquid can be added, whereby layer 3) will swell and add a light pressure down towards the stung area. This will improve the contact with the skin and provide a faster transport of the poison from the skin into layer 5).
2) Liquid-permeable membrane, which allows liquid to penetrate into layer 3)
3) Swell layer consisting of a material, which swells at the addition of water or another liquid.
4) Membrane, which separates layer 3) from layer 5).
5) Matrix layer containing an expulsion agent, which may be a carbohydrate selected from the group consisting of sucrose, glucose, dextrose, maltose, honey, or another kind of carbohydrate or another kind of poison-expulsion agent.
6) An optional permeable membrane consisting of gauze or the like, which allows the poison from the bee sting to penetrate into layer 5). Simultaneously, the membrane encases, potentially together with membrane (4), completely or partly the matrix.
7) The patch seen from below. An adhesive added or an adhesive layer laminated to the outer layer (1), which sticks the patch to the skin. A centre patch hole is to be placed on top of the stung area.

EXAMPLES

Example 1

A patch designed as illustrated in FIG. 1, where
the matrix consists of cotton containing sugar crystals
the swell layer is a silica gel

Example 2

A patch designed according to example 1 to which water is added through a hole designed for that purpose in the upper layer of the patch. Thereby the depth of the swell layer is increased.

Example 3

A patch designed according to example 1 is fixed to a fresh bee sting. An equivalent patch with a matrix without an expulsion agent is fixed to another fresh bee sting. After the fixing of the patch, the time at which relief is experienced occurs sooner with the patch according to example 1 than with the patch without an expulsion agent.

Example 4

A patch designed according to example 1 is fixed to a fresh bee sting. A sugar cube is fixed to another fresh bee sting. The time at which relief is experienced is sooner with the patch according to example 1 than with the sugar cube.

Example 5

A patch designed as illustrated in FIG. 1, where
the matrix consists of cotton containing sugar crystals and lidocaine
the swell layer is a silica gel

The invention claimed is:

1. A patch, comprising:
an outer layer having a top side, an underside and one or more openings between the top side and the underside, the top side facing away from the skin of a user when in use and the underside comprising an adhesive or an adhesive layer on at least a part of the underside in contact with the skin of the user when in use;
a first permeable membrane that allows liquid to penetrate into a subjacent swell layer;
a swell layer that swells and increases its depth with the addition of water or another liquid;
a membrane that separates the swell layer from a subjacent matrix layer;
a matrix layer comprising an osmotically active poison-expelling agent;
a second permeable membrane that allows the insect poison to penetrate into the matrix layer and which, together with the membrane, fully or partly encases the matrix layer; and
a removable protective layer, wherein the outer layer is larger than and covers the first permeable membrane, the swell layer, the membrane, the matrix layer, the second permeable membrane and the removable protective layer and wherein a liquid can be added to one or more subjacent layers through the one or more openings of the outer layer.

2. The patch according to claim 1, wherein the matrix layer comprises local anesthetics selected from the group consisting of: lidocaine, benzocaine, procaine, xylocaine, and combinations thereof.

3. The patch according to claim 1, wherein the poison-expelling agent in the matrix layer comprises a carbohydrate selected from the group consisting of: sucrose, glucose, dextrose, maltose, honey, and combinations thereof.

4. The patch according to claim 1, wherein the swell layer consists of a material selected from the group consisting of silica gel, compressed cellulose, calcium chloride and combinations thereof.

5. The patch according to claim 1 for the expulsion of insect poison from stings by membranous insects.

6. A method of treatment of humans and animals for the expulsion of insect poison from stings by membranous insects, comprising:
applying a patch comprising:
an outer layer having a top side, an underside and one or more openings between the top side and the underside, the top side facing away from the skin of a user when in use and the underside comprising an adhesive or an adhesive layer on at least a part of the underside in contact with the skin of the user when in use;
a first permeable membrane that allows liquid to penetrate into a subjacent swell layer;
a swell layer that swells and increases its depth with the addition of water or another liquid;
a membrane that separates the swell layer from a subjacent matrix layer;
a matrix layer comprising an osmotically active poison-expelling agent;
an optional second permeable membrane, which allows the insect poison to penetrate into the matrix layer and which, together with the membrane, fully or partly encases the matrix layer, wherein the outer layer is larger than and covers the first permeable membrane, the swell layer, the membrane, the matrix layer and the second permeable membrane and wherein a liquid can be added to one or more subjacent layers through the one or more openings of the outer layer.

7. The method according to claim 6, wherein the matrix layer of the patch comprises local anesthetics selected from the group consisting of: lidocaine, benzocaine, procaine, xylocaine, and combinations thereof.

8. The method according to claim 6, wherein the poison-expelling agent in the matrix layer comprises a carbohydrate selected from the group consisting of sucrose, glucose, dextrose, maltose, honey, and combinations thereof.

9. The method according to claim. 6, wherein the swell layer consists of a material selected from the group consisting of silica gel, compressed cellulose, calcium chloride and combinations thereof.

* * * * *